United States Patent [19]

Caton et al.

[11] 4,036,872
[45] July 19, 1977

[54] CYCLOPENTANE DERIVATIVES

[75] Inventors: Michael Peter Lear Caton, Upminster; Edward Charles John Coffee, London; Gordon Leonard Watkins, Hornchurch, all of England

[73] Assignee: May & Baker Limited, Dagenham, England

[21] Appl. No.: 523,015

[22] Filed: Nov. 12, 1974

[30] Foreign Application Priority Data

Nov. 13, 1973  United Kingdom ............... 52695/73

[51] Int. Cl.² .......................................... C07C 177/00
[52] U.S. Cl. ............................ 260/468 D; 260/340.9; 260/488 R; 260/514 D; 424/305; 424/317
[58] Field of Search ....... 260/468 D, 514 D, 514 CA; 424/305, 317

[56] References Cited

U.S. PATENT DOCUMENTS 3,816,393   6/1974   Hayashi et al. ...................... 260/209

FOREIGN PATENT DOCUMENTS 784,809   12/1972   Belgium ............................. 260/468

OTHER PUBLICATIONS

Karim, Prostaglandins pp. 313–315 (1972).

Primary Examiner—Robert Gerstl
Attorney, Agent, or Firm—Stevens, Davis, Miller & Mosher

[57] ABSTRACT

Cyclopentane derivatives of the formula:

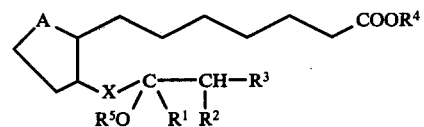

wherein $R^1$ represents alkyl of 1 through 4 carbon atoms, $R^2$ represents hydrogen or alkyl of 1 through 3 carbon atoms, $R^3$ represents alkoxy of 3 through 6 carbon atoms, or alkoxyalkyl in which alkoxy and alkyl moieties each contain 1 through 4 carbon atoms, $R^4$ represents hydrogen or alkyl of 1 through 12 carbon atoms, $R^5$ represents hydrogen or alkyl of 1 through 4 carbon atoms or a carboxylic acyl group, A represents carbonyl or a group $-CH(OR^5)-$ wherein $R^5$ is as hereinbefore defined, and X represents ethylene or trans-vinylene, possess pharmacological properties, for example the production of hypotension, broncodilation, inhibition of gastric acid secretion, and stimulation of uterine contraction.

9 Claims, No Drawings

CYCLOPENTANE DERIVATIVES

This invention relates to new therapeutically useful cyclopentane derivatives, a process for preparing them and to pharmaceutical compositions containing them.

The new cyclopentane derivatives of the present invention are those compounds of the general formula:

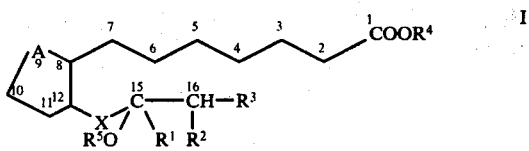

[wherein $R^1$ represents a straight- or branched-chain alkyl group containing 1 to 4 carbon atoms, $R^2$ represents a hydrogen atom or a straight- or branched-chain alkyl group containing from 1 to 3 carbon atoms, preferably a methyl group, $R^3$ represents a straight- or branched-chain alkoxy group containing from 3 to 6 carbon atoms or a straight- or branched-chain alkoxyalkyl group (wherein the alkoxy and alkyl moieties each contain from 1 to 4 carbon atoms), $R^4$ represents a hydrogen atom or a straight- or branched-chain alkyl group containing from 1 to 12 carbon atoms, $R^5$ represents a hydrogen atom or a straight- or branched-chain alkyl group containing from 1 to 4 carbon atoms or a carboxylic acyl group, for example a straight- or branched-chain alkanoyl group containing from 1 to 4 carbon atoms, A represents a carbonyl group or a group —CH($OR^5$)— wherein $R^5$ is as hereinbefore defined, and X represents an ethylene group or, preferably a transvinylene group] and, where $R^4$ represents a hydrogen atom, non-toxic salts thereof.

As will be apparent to those skilled in the art, the compounds of general formula I have at least three centres of chirality, these three centres of chirality being at the carbon atoms in positions 8, 12 and 15. In addition to these three centres of chirality, a further centre of chirality will occur when $R^2$ represents an alkyl group (at the carbon atom in position 16) and still further centres of chirality may occur in the groups $R^1$ and $R^3$. The presence of centres of chirality, as is well known, leads to the existence of isomerism. However, the compounds of general formula I all have such a configuration that the side chains attached to the ring carbon atoms in positions 8 and 12 are trans with respect to each other. Accordingly, all isomers of general formula I, and mixtures thereof, which have those side chains, attached to the ring carbon atoms in positions 8 and 12, in the trans-configuration are within the scope of the present invention. Preferably the groups attached to the 8 and 12 positions of the cyclopentane ring are in the same configurations as those in the natural products known as prostaglandins, viz. alpha and beta respectively.

The compounds of the invention and non-toxic salts thereof possess valuable pharmacological properties, for example, properties typical of the related series of natural products known as prostaglandins including, for example, the production of hypotension, bronchodilatation, inhibition of gastric acid secretion, and stimulation of uterine contraction.

In a laboratory screening test the compounds produced an inhibition of pentagastrin-inducted gastric acid secretion in the rat at doses of between 1.0 and 100 μg./kg. animal body weight/minute when administered orally in solution in an aqueous sodium chloride solution.

In another laboratory test, the effects of aerosols containing compounds of the invention were observed in conscious guinea pigs. Thus, guinea pigs were continuously exposed to an aerosol containing a compound of the invention for a period of 3 minutes. After a pause of 30 seconds, the animals were exposed to an aerosol of the bronchoconstrictor histamine generated from a solution of histamine in water (2 mg./ml.) and the time taken for convulsions to occur (termined the "preconvulsion time") was noted. For example, the preconvulsion time obtained in animals pre-treated with an aerosol generated from a solution containing 500 μg./ml. of 7-[5-(3-hydroxy-3-methyl-4-propoxybut-1-enyl)-2-oxocyclopentyl]heptanoic acid, compared with the preconvulsion time obtained in control animals pretreated with a similar aerosol from which the compound of the invention was absent, showed an increase of 83% in the preconvulsion time.

Classes of compounds of general formula I of particular importance are those a. wherein $R^5$ represents a hydrogen atom, A represents a carbonyl group, X represents a trans-vinylene group and $R^1$, $R^2$, $R^3$ and $R^4$ are as hereinbefore defined, and especially those compounds wherein $R^3$ represents an alkoxy group containing 3 carbon atoms or an alkoxyalkyl group containing 3 carbon atoms;

b. wherein $R^1$ represents a methyl group, $R^2$ represents a hydrogen atom, $R^3$ represents an alkoxy group containing 3 carbon atoms or an alkoxyalkyl group containing 3 carbon atoms, and $R^4$, $R^5$, A and X are as hereinbefore defined;

c. wherein X represents an ethylene group, and $R^1$, $R^2$, $R^3$, $R^4$, $R^5$ and A are as hereinbefore defined; and d. wherein A represents a group —CH($OR^5$)—, and $R^1$, $R^2$, $R^3$, $R^4$, $R^5$ and X are as hereinbefore defined.

According to a feature of the present invention, the cyclopentanone compounds of formula I wherein $R^4$ and $R^5$ both represent hydrogen atoms, A represents a carbonyl group, and X represents a trans-vinylene group, $R^1$, $R^2$ and $R^3$ being as hereinbefore defined (hereinafter referred to as "compounds of formula Ia") are prepared by the process which comprises reacting a compound of general formula II or III:

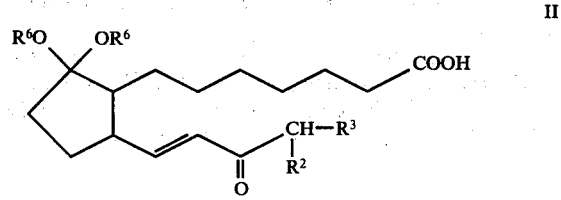

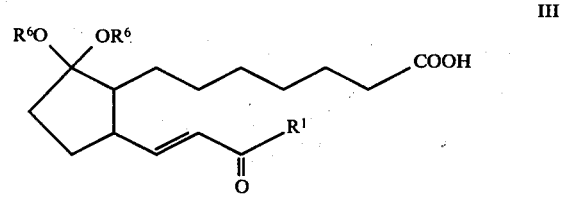

(wherein $R^1$, $R^2$ and $R^3$ are as hereinbefore defined and the symbols $R^6$ represent identical alkyl groups or together form an ethylene linkage unsubstituted or substituted by identical alkyl groups on each carbon atom, the symbols $R^6$ preferably representing together an unsubstituted ethylene linkage), or such a compound in which the carboxy group (i.e. —COOH) is protected so as to be relatively inert to Grignard reagents and is readily hydrolyzable back to carboxy, with a Grignard reagent which may be represented by general formula IV or V respectively:-

   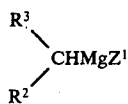

IV    V (wherein $R^1$, $R^2$ and $R^3$ are as hereinbefore defined and $Z^1$ represents a halogen atom, preferably a bromine, or more expecially, iodine atom), and hydrolyzing the compound so obtained. As is well known, carboxy groups - as well as carbonyl groups - react with Grignard reagents and so it is preferable, therefore, to protect the carboxy group of the acid of formula II or III before effecting the Grignard reaction. This is generally carried out by conversion of the carboxy group to a group —$COOQ^1$ which is relatively inert to Grignard reagents but is readily hydrolyzed back to a carboxy group when desired. Suitably $Q^1$ represents a trialkylsilyl group, preferably a trimethylsilyl group which may be introduced by the reaction of the compound of formula II or III with hexamethyldisilazane, in the presence of trimethylchlorosilane or hydrogen chloride gas, in dry conditions, for example in dry tetrahydrofuran as solvent.

The Grignard reaction is carried out in conditions typical of Grignard reactions, for example in an ether (e.g. diethyl ether) at or near room temperature, to form, for example, an intermediate of the general formula:

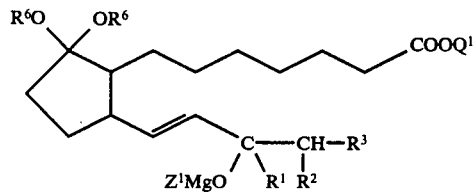

wherein $R^1$, $R^2$, $R^3$, $R^6$, $Q^1$ and $Z^1$ are as hereinbefore defined.

The intermediate compound of formula VI, generally without isolation, is then converted to a cyclopentanone compound of formula Ia by hydrolysis. Mild hydrolysis often yields a ketal of the general formula:

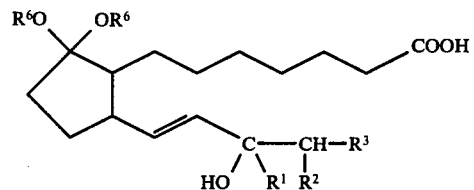

(wherein $R^1$, $R^2$, $R^3$ and $R^6$ are as hereinbefore defined), which may then be converted to the cyclopentanone of formula Ia by acid hydrolysis, usually by means of an organic acid in the presence of water, for example acetic acid, e.g. 80% v/v aqueous or glacial acetic acid, or p-toluenesulphonic acid in acetone containing a small amount of water, preferably at temperatures between 520 and 100° C., more particularly between 15° and 30° C. Alternatively the ketal of formula VII may be converted to the cyclopentanone of formula Ia by subjecting it to chromatography, preferably using an eluant containing some glacial acetic acid. By this means purification is effected simultaneously with hydrolysis.

The compounds of formulae II and III may be prepared by the reaction sequence illustrated schematically as follows:

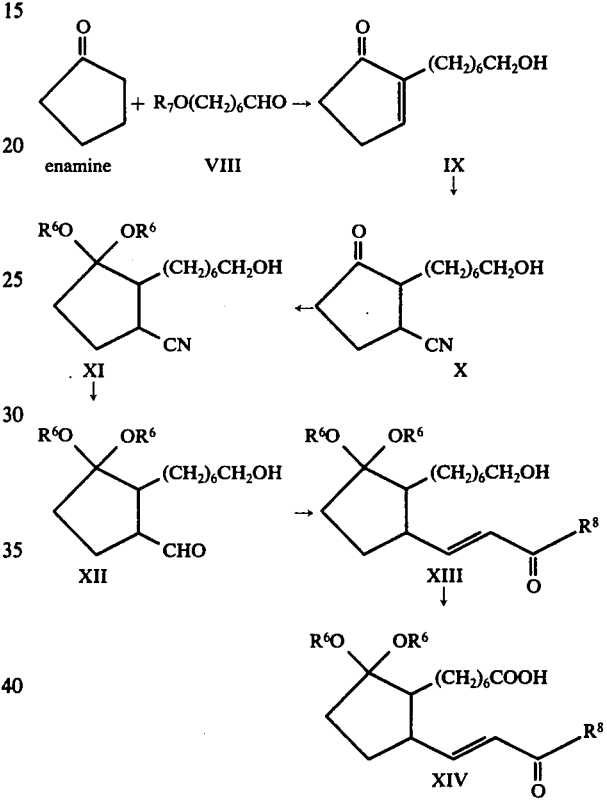

wherein $R^6$ is as hereinbefore defined, $R^7$ represents a hydrogen atoms or a suitable acid labile group and $R^8$ represents a group —$CH(R^2)R^3$ or $R^1$, wherein $R^1$, $R^2$ and $R^3$ are as hereinbefore defined. Suitable acid labile groups represented by $R^7$ are those which are easily removed by acid hydrolysis and do not cause side reactions, e.g. the 2-tetrahydropyranyl group unsubstituted or substituted by, for example, at least one lower alkyl group.

The reaction of an aldehyde of formula VIII and an enamine (e.g. the morpholine enamine) of cyclopentanone to yield an alcohol of formula IX is carried out in an inert organic solvent, for example an aromatic hydrocarbon (e.g. benzene) with continuous removal of water, preferably at 60°-120° C., followed by hydrolysis in aqueous acid conditions (e.g. with hydrochloric acid), preferably at ambient temperature, and then heating with an acid (e.g. concentrated hydrochloric acid), preferably at about 100° C., and preferably in an inert organic solvent such as an alcohol (e.g. butanol) to cause the double bond to migrate from the exocyclic to the endocyclic position.

The alcohols of general formula IX are reacted with a source of hydrogen cyanide (e.g. acetone cyanohydrin) preferably in the presence of a base, for example an alkali metal carbonate (e.g. sodium carbonate), in an aqueous organic solvent, for example an aqueous lower alkanol (e.g. aqueous methanol), preferably at 50°–110° C. and advantageously at the reflux temperature of the solvent employed, to give ketonitriles of formula X.

The ketals of general formula XI are prepared from the ketonitriles of formula X by the application or adaptation of know methods for the preparation of ketals from ketones, for example by the reaction of a compound of formula X with the appropriate alcohol or diol in the presence of an acidic catalyst, for example p-toluene-sulphonic acid, with continuous removal of water. Advantageously the reaction is effected in the presence of an inert organic solvent, for example an aromatic hydrocarbon (e.g. benzene), at an elevated temperature, with continuous removal of water by means of a Dean and Stark apparatus.

The ketals of general formula XI are reduced in an inert organic solvent, for example a lower dialkyl ether (e.g. diethyl ether), preferably at a temperature between −80° C. and +30° C., to compounds of formula XII by means of known complex metal reducing agents, preferably a dialkylaluminium hydride (e.g. diisobutylaluminium hydride) in an inert organic solvent, for example an aromatic hydrocarbon (e.g. benzene).

Compounds of formula XIII are prepared by the reaction of compounds of formula XII, either with compounds of the general formula:

$$(R^9)_3P=CHCOR^8 \qquad XV$$

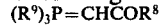

(wherein $R^8$ is as hereinbefore defined, and $R^9$ represents an alkyl group of from 1 to 6 carbon atoms or a phenyl group unsubstituted or substituted by an alkyl group, and advantageously represents a phenyl or n-butyl group), preferably in the presence of an inert organic solvent and preferably at a temperature between 20° and 100° C., for example in the presence of tetrahydrofuran as solvent at the reflux temperature of the reaction mixture or in the presence of hexamethylphosphotriamide as solvent at between 95° and 100° C., or preferably with compounds of the general formula:

$$(R^{10}O)_2P(O)CH_2COR^8 \qquad XVI$$

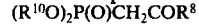

(wherein $R^8$ is as hereinbefore defined and $R^{10}$ represents an alkyl group of from 1 to 4 carbon atoms, preferably a methyl group), in the presence of a strong base, for example sodium hydride, and preferably in the presence of an inert organic solvent, for example an ether (e.g. tetrahydrofuran), and preferably at or near room temperature.

The compounds of formula XIII are then oxidised, preferably in an inert organic solvent, by means of an agent known to convert a terminal hydroxymethyl group to carboxy without affecting carbon-carbon double bonds or the group

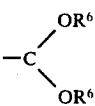

(for example chromium trioxide and sulphuric acid in dimethylformamide, preferably at a temperature of −5° to +10° C.) to give the compounds of formula XIV.

Compounds of formula XV may be prepared by the application or adaptation of known methods, for example by the reaction between compounds of the general formula:

$$Z^2CH_2COR^8 \qquad XVII$$

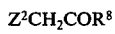

(wherein $R^8$ is as hereinbefore defined and $Z^2$ represents a bromine or chlorine atom) and an appropriate trialkyl- or triphenyl-phosphine in a suitable organic solvent (e.g. chloroform) under a nitrogen atmosphere, preferably at a temperature of 20°–100° C. and advantageously at the reflux temperature of the reaction mixture, followed by reaction of the resulting 2-oxoalkyl-phosphonium halide with an inorganic base (e.g. aqueous sodium carbonate) at ambient temperature.

Compounds of formula XVI may be prepared by the application or adaptation of known methods, for example by the treatment of a compound of the general formula:

$$(R^{10}O)_2P(O)CH_3 \qquad XVIII$$

(wherein $R^{10}$ is as hereinbefore defined) with butyl lithium at a low temperature, e.g. between −45° C. and −60° C., and in an inert organic solvent, e.g. a mixture of tetrahydrofuran and hexane, preferably under a nitrogen atmosphere, followed by treatment of the resulting mixture, containing a compound of the general formula:

$$(R^{10}O)_2P(O)CH_2Li \qquad XIX$$

(wherein $R^{10}$ is as hereinbefore defined), with a compound of the general formula:

$$R^{11}OOCR^8 \qquad XX$$

(wherein $R^8$ is as hereinbefore defined and $R^{11}$ represents an alkyl, preferably ethyl or propyl, group) at a temperature initially between −70° C. and −55° C. and subsequently rising to room temperature.

Compounds of formulae XVII and XX may be prepared by the application or adaptation of known methods.

According to a further feature of the present invention, the cyclopentanone compounds of formula Ia are converted to compounds of formula I wherein $R^1$, $R^2$, $R^3$, $R^4$, $R^5$, A and X are as hereinbefore defined but wherein one or more of the symbols $R^4$, $R^5$, A and X have the following significances:

a. $R^4$ represents a straight- or branched-chain alkyl group containing from 1 to 12 carbon atoms;

b. A represents a group —CH(OR$^5$) wherein $R^5$ is as hereinbefore defined;

c. $R^5$ represents a straight- or branched-chain alkyl group containing from 1 to 4 carbon atoms or a carboxylic acyl group, for example a straight- or branched-chain alkanoyl group containing from 1 to 4 carbon atoms;

d. X represents an ethylene group; or to salts of compounds of formula I wherein $R^4$ represents a hydrogen atom, by the application or adaptation of known methods of preparing esters from acids, of preparing ethers or esters from alcohols, of preparing alcohols from ketones, of reducing carbon-carbon double bonds, or of preparing salts from acids.

Thus, (1) compounds of general formula I in which $R^4$ represents an alkyl group can be prepared by the reaction of a corresponding carboxylic acid of general formula I in which $R^4$ represents a hydrogen atom with an alcohol of the general formula:

$$R^{12}OH \qquad\qquad XXI$$

(wherein $R^{12}$ represents a straight- or branched-chain alkyl group containing from 1 to 12 carbon atoms), an excess of which may be employed as solvent medium, in the presence of an inorganic acid, e.g. hydrochloric acid or sulphuric acid, preferably at a temperature between 50° and 160° C., and advantageously at the reflux temperature of the reaction mixture, or, where $R^{12}$ can be represented by the formula $-CHR^{13}R^{14}$ [wherein the symbols $R^{13}$ and $R^{14}$ are identical or different and each represents an alkyl group (the total number of carbon atoms in the two groups $R^{13}$ and $R^{14}$ being at most 11) or, preferably, a hydrogen atom], with a diazoalkane of the general formula:

$$R^{13}R^{14}C=N_2 \qquad\qquad XXII$$

(wherein $R^{13}$ and $R^{14}$ are as hereinbefore defined) in an inert organic solvent medium, preferably a dialkyl ether (e.g. diethyl ether), preferably at ambient temperature. Alternatively, a silver salt of such a carboxylic acid of formula I can be reacted with an alkyl halide $R^{12}Z^3$, wherein $Z^3$ represents a halogen atom and $R^{12}$ is as hereinbefore defined, optionally in the presence of an inert organic solvent such as an aromatic hydrocarbon (e.g. benzene) at elevated temperatures and advantageously at the reflux temperature of the reaction mixture, or a sodium salt of a said carboxylic acid of formula I can be reacted with a said alkyl halide in a polar solvent, such as hexamethylphosphotriamide, preferably at room temperature.

2. Compounds of general formula I wherein $R^5$ represents a straight- or branched-chain alkyl group and $R^4$ represents an alkyl group can be prepared by the reaction of a compound of the formula $R^{15}Y$ (wherein $R^{15}$ represents a straight- or branched-chain alkyl group containing from 1 to 4 carbon atoms and Y represents the acid residue of a reactive ester, e.g. a bromine, chlorine or iodine atom or a sulphonate or sulphate group) with a compound of formula I wherein $R^5$ represents a hydrogen atom, optionally in an inert organic solvent, for example an aromatic hydrocarbon (e.g. benzene), in the presence of an alkali metal or alkaline earth metal hydride (e.g. sodium hydride) or a suitable metal oxide, preferably silver oxide, preferably at a temperature of 50°–150° C. Alternatively a compound of formula I wherein $R^5$ represents a hydrogen atom can be reacted with a diazoalkane of the formula $R^{16}=N_2$ (wherein $R^{16}$ represents an alkylidene group containing from 1 to 4 carbon atoms) and a Lewis acid, e.g. boron trifluoride, in an inert organic solvent medium, preferably a dialkyl ether (e.g. diethyl ether), and preferably at a temperature between $-50°$ and $-20°$ C. to give compounds of general formula I wherein $R^5$ represents an alkyl group.

The products so obtained can, if desired, be hydrolysed, for example with an aqueous alkali (e.g. aqueous sodium hydroxide), preferably at a temperature of 40°–110° C., to give the corresponding free acids of general formula I wherein $R^4$ represents a hydrogen atom.

3. Compounds of general formula I wherein $R^5$ represents a carboxylic acyl group can be prepared by the reaction of a corresponding compound of general formula I, wherein $R^5$ represents a hydrogen atom, with a carboxylic acid anhydride of the formula $(R^{17})_2O$ (wherein $R^{17}$ represents a carboxylic acyl group) such as acetic anhydride, preferably in the presence of a base, e.g. pyridine, preferably at ambient temperature, optionally in the presence of an inert organic solvent such as an aromatic hydrocarbon (e.g. benzene).

Compounds of formula I wherein X and A do not simultaneously represent a trans-vinylene group and a carbonyl group respectively (hereinafter referred to as "compounds of formula Ib") are prepared by the reduction of compounds of formula I wherein X and A do not simultaneously represent an ethylene group and a hydroxymethylene group respectively (hereinafter referred to as "compounds of formula Ic"). Thus:

4a. Compounds of formula Ib wherein X represents an ethylene or trans-vinylene group and A represents a hydroxymethylene group are prepared by reduction of the corresponding compounds of formula Ic wherein X represents an ethylene or trans-vinylene group and A represents a carbonyl group, using means and conditions capable of reducing carbonyl groups to hydroxymethylene groups without affecting carbon-carbon double bonds. The reduction is preferably effected by a metal borohydride (e.g. sodium borohydride or potassium borohydride), usually in an aqueous, alcoholic or aqueous alcoholic medium and at between $-40°$ and $+30°$ C., preferably between $-5°$ and $+15°$ C., optionally in the presence of a base, for example an alkali metal hydroxide (e.g. aqueous sodium hydroxide or aqueous potassium hydroxide) or, especially when potassium borohydride is employed, in aqueous or aqueous alcoholic conditions buffered at a pH of from pH 7 to pH 9, e.g. at pH 8 (e.g. by the addition of aqueous citric acid solution). Alternatively the reduction is carried out by reaction with aluminum isopropoxide, in the presence of isopropanol, preferably as the solvent medium, at an elevated temperature, advantageously at the reflux temperature of the reaction mixture.

4b. Compounds of formula Ib wherein X represents an ethylene group and A represents a carbonyl or hydroxymethylene group are prepared by reduction of the corresponding compounds of formula Ic wherein X represents a trans-vinylene group and A represents a carbonyl or hydroxymethylene group, with means and in conditions capable of reducing carbon-carbon double bonds without affecting carbonyl groups. The reduction is preferably effected by hydrogenation in the presence of a hydrogenation catalyst, for example rhodium on charcoal, in the presence of an inert organic solvent, for example a lower alkanol, e.g. ethanol, generally at ambient temperature and elevated pressure, e.g. at a hydrogen pressure of 15 kilograms per square centimetre.

4c. Compounds of formula Ib wherein X represents an ethylene group and A represents a hydroxymethylene group are prepared by reduction of corresponding compounds of formula Ic with means and in conditions capable of reducing any carbonyl groups present to hydroxymethylene groups and any vinylene groups present to ethylene groups. The reduction is preferably effected by hydrogenation in the presence of a hydrogenation catalyst, for example palladium on charcoal, in the presence of an inert organic solvent, for example a lower alkanol, e.g. ethanol, preferably at an elevated pressure, e.g. at a hydrogen pressure of 15 kilograms per square centimetre.

By the term "non-toxic salts" is meant salts the cations of which are relatively innocuous to the animal organism when used in therapeutic doses so that the beneficial pharmacological properties of the parent compound of the invention are not vitiated by side-effects ascribable to those cations. Preferably, the salts are water-soluble. Suitable salts include the alkali metal, e.g. sodium or potassium, and ammonium salts and pharmaceutically-acceptable (i.e. non-toxic) amine salts.

Amines suitable for forming such salts with carboxylic acids are well known and include, for example, amines derived in theory by the replacement of one or more of the hydrogen atoms of ammonia by groups, which may be the same or different when more than one hydrogen atom is replaced, selected from alkyl groups containing from 1 to 6 carbon atoms, hydroxyalkyl groups containing from 1 to 3 carbon atoms, cycloalkyl groups containing from 3 to 6 carbon atoms, phenyl groups, phenylalkyl groups containing from 7 to 11 carbon atoms and phenylalkyl groups containing from 7 to 15 carbon atoms wherein the alkyl moieties are substituted by hydroxy groups. The phenyl groups and phenyl moieties of such phenylalkyl groups may be unsubstituted or substituted by one or two alkyl groups containing from 1 to 6 carbon atoms. Suitable amines also include those derived in theory by the replacement of two of the hydrogen atoms of ammonia by a hydrocarbon chain, which may be interrupted by nitrogen, oxygen or sulphur atoms, to form, together with the nitrogen atom of ammonia to which its terminal groups are attached, a five- or six-membered nitrogen-containing heterocyclic ring, which heterocyclic ring may be unsubstituted or substituted by one or two alkyl groups containing from 1 to 6 carbon atoms. Examples of suitable amine cations include mono-, di- and tri- methylammonium, mono-, di- and tri-ethylammonium, mono-, di- and tri-propylammonium, mono-, di- and triisopropylammonium, ethyldimethylammonium, mono-, di- and tri-2-hydroxyethylammonium, ethylbis(2-hydroxyethyl)-ammonium, butylmono(2-hydroxyethyl)ammonium, tris(hydroxymethyl)methylammonium, cyclohexylammonium, benzylammonium, benzyldimethylammonium, dibenzylammonium, phenyl-2-hydroxyethylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-butylpiperidinium, 2-methylpiperidinium and 1-ethyl-2-methylpiperidinium.

The non-toxic salts may be prepared from parent compounds of formula I by known methods, for example by reaction of stoichiometric quantities of compounds of formula I (wherein $R^4$ represents a hydrogen atom) and the appropriate base, e.g. an alkali metal hydroxide or carbonate, ammonium hydroxide, ammonia or an amine, in a suitable solvent which is preferably water in the case of the preparation of alkali metal salts and water or isopropanol in the case of amine salts. The salts may be isolated by lyophilisation of the solution or, if sufficiently insoluble in the reaction medium, by filtration, if necessary after removal of part of the solvent.

As well as being useful in themselves as pharmaceutically useful compounds, salts of the compounds of formula I wherein $R^4$ represents a hydrogen atom are useful for the purpose of purification of the parent acids of formula I, for example by exploitation of the solubility differences between the salts and the parent acids in water and in organic solvents, by techniques well known to those skilled in the art. The parent acids of formula I can be regenerated from their salts by known methods, for example by treatment with a mineral acid, e.g. dilute hydrochloric acid.

It is to be understood that where in this specification reference is made to compounds of formula I, or to compounds of the invention, it is intended to refer also, where the context so permits, to the said salts of the compounds of formula I wherein $R^4$ represents a hydrogen atom.

By the term "known methods" as used in this specification is meant methods heretofore used or described in the literature.

As will be readily appreciated by those skilled in the art, the isomeric forms of the compounds of the invention arising from the aforementioned centres of chirality may be separated by the application or adaptation of known methods, for example diastereoisomeric forms may be separated by chromatography using selective adsorption from solution or from the vapour phase onto suitable adsorbents, and enantiomeric forms of compounds of the invention wherein $R^4$ represents a hydrogen atom may be separated by formation of salts with an optically active base, followed by separation of the obtained pair of diastereoisomers by, for example, fractional crystallisation from a suitable solvent system, followed by separate regeneration of the enantiomeric acids.

The following Examples illustrate the preparation of new compounds of the present invention.

EXAMPLE 1

7-[5-Hydroxy-3-methyl-4-propoxybut-1-enyl)-2-oxocyclopentyl]heptanoic acid.

i. Preparation of 2-(7-hydroxyheptyl)cyclopent-2-en-1-one

A mixture of 7-(2-tetrahydropyranyloxy)heptanal (22 g.) and 1-morpholinocyclopentene, i.e. the morpholine enamine of cyclopentanone, (21.4 g.) in benzene (25 ml.) was heated under reflux for 12 hours under nitrogen, and the water liberated was continuously removed with a Dean and Stark head. Benzene (10 ml.) and then, dropwise, 18% hydrochloric acid (28 ml.) were added and the mixture was stirred for 2 hours. The organic layer was separated and evaporated. Concentrated hydrochloric acid (72 ml.) and butanol (300 ml.) were added to the residue. The mixture was heated at 100° C. for 1 hour, and then the solution was concentrated to give an oil. Diethyl ether was added, and the ether solution was washed with aqueous sodium bicarbonate and then water, and dried over sodium sulphate. The solvent was evaporated and the residue was distilled under reduced pressure to give 2-(7-hydroxyheptyl)cyclopent-2-en-1-one (11.7 g.), b.p. 125°–170° C./0.15 mm.Hg, $n_D^{25}$ 1.490, $\lambda_{max}$ 228 m$\mu$ (ethanol).

The 7-(2-tetrahydropyranyloxy)heptanal used as starting material in the above procedure was prepared as follows:

3,4-Dihydro-2H-pyran (272 g.) was added dropwise at 40° C. with stirring to a mixture of 7-hydroxyheptanenitrile (284 g.) and concentrated hydrochloric acid (10 drops). The temperature was allowed to rise to 65° C. and was maintained at this level for one hour. The solution was cooled and benzene (500 ml.) was added. The solution was washed with aqueous sodium bicarbonate and then water, and dried over sodium sulphate. The solvent was removed in vacuo, and the residue distilled under reduced pressure to give 7-(2-tetrahydropyranyloxy)heptanenitrile (411 g.), b.p. 100°–130° C./0.1 mm.Hg, $n_D^{25}$ 1.455.

Diisobutylaluminium hydride (19.4 g.) in dry benzene (50 ml.) was added dropwise at 10° C. to a stirred solution of 7-(2-tetrahydropyranyloxy)heptanenitrile (20.6 g.) in dry diethyl ether (200 ml.). The solution was stirred at 10° C. for 30 minutes and was then added to 2N aqueous sulphuric acid (300 ml.) at 0° C. The mixture was heated at 30° C. for 30 minutes, and then saturated with sodium chloride and the layers were separated. The aqueous layer was extracted with diethyl ether and the combined organic layers were washed with aqueous sodium bicarbonate, and then aqueous sodium chloride, and dried over sodium sulphate. The solvent was evaporated and the residue was distilled under reduced pressure to give 7-(2-tetrahydropyranyloxy)-heptanal (12.7 g.), b.p. 78°–106° C./0.1 mm.Hg, $n_D^{25}$ 1.456.

ii. Preparation of 2-(7-hydroxyheptyl)-3-oxocyclopentanecarbonitrile

A mixture of 2-(7-hydroxyheptyl)cyclopent-2-en-1-one (17 g.), acetone cyanohydrin (8.5 g.), 6% aqueous sodium carbonate (8 ml.) and methanol (50 ml.) was stirred and heated under reflux for 4 hours. Methanol was removed in vacuo, water (100 ml.) was added and the mixture was extracted with diethyl ether and the extract dried over magnesium sulphate. The solvent was removed by evaporation, and the residue was distilled under reduced pressure to give 2-(7-hydroxyheptyl)-3-oxocyclopentanecarbonitrile (13.3 g.), b.p. 144°–182° C./0.15 mm.Hg, $n_D^{25}$ 1.4795.

iii. Preparation of 7-cyano-6-(7-hydroxyheptyl)-1,4-dioxaspiro[4,4]nonane

A mixture of 2-(7-hydroxyheptyl)-3-oxocyclopentanecarbonitrile (20 g.), ethylene glycol (5.6 g.), p-toluenesulphonic acid (1 g.) and benzene 160 ml.) was heated to reflux for 210 minutes with continuous removal of water. The mixture was cooled to ambient temperature, anhydrous sodium carbonate was added and, after filtration through a bed of sodium carbonate, the solvent was removed under reduced pressure. The residue was distilled under reduced pressure to give 7-cyano-6-(7-hydroxyheptyl)-1,4-dioxaspiro[4,4]nonane (19.3 g.), b.p. 166° C–182° C./0.1 mm.Hg. This material was used as a starting material in the next stage, as aliquot being redistilled to b.p. 177°–179° C./0.1 mm.Hg for elemental analysis:

Found C, 67.1; H, 9.2; N, 4.89% $C_{15}H_{25}NO_3$ requires: C, 67.37; H, 9.42; N, 5.24%.

Preparation of 7-formyl-6-(7-hydroxyheptyl)-1,4-dioxaspiro[4,4]nonane

A solution of diisobutylaluminium hydride (53 g.) in dry benzene (145 ml.) was added, with rapid stirring, to a solution of 7-cyano-6-(7-hydroxyheptyl)-1,4-dioxaspiro[4,4]nonane (43.2 g.) in dry diethyl ether (432 ml.) at 10°–15° C. Stirring at ambient temperature was continued for 90 minutes and the mixture was added to 2N aqueous acetic acid (1 litre) at a temperature lower than 15° C. The organic phase was separated and the aqueous layer was extracted with diethyl ether. The combined organic phases were washed with aqueous sodium bicarbonate, dried over sodium sulphate, the solvents removed in vacuo and the residue distilled under reduced pressure to give 7-formyl-6-(7-hydroxyheptyl)-1,4-dioxaspiro[4,4]nonane (25.3 g), b.p. 164°–200° c./0.05 mm.Hg,$v_{max}$ 1710 cm$^{-1}$, 2700 cm$^{-1}$ (liquid film).

v. Preparation of 6-(7-hydroxyheptyl)-7-(3-oxo-4-propoxybut-1-enyl)-1,4-dioxaspiro[4,4]nonane A mixture of 7-formyl-6-(7- hydroxyheptyl)-1,4-dioxaspiro[4,4]nonane (4.2 g.) and propoxyacetylmethylenetriphenylphosphorane (7.18 g) in dry tetrahydrofuran (35 ml.) was heated at reflux under nitrogen for 18 hours. The solvent was removed in vacuo and the residue triturated with a mixture of petroleum ether (b.p. 60°–80° C.) and ethyl acetate, allowed to stand at 0° C., filtered to remove triphenylphosphine oxide and the filtrate evaporated to dryness to give 6-(7-hydroxyheptyl -7-(3-oxo-4- propoxybut-1-enyl)-1,4-dioxaspiro[4,4]-nonane (8.6 g.) $v_{max}$ 1620 cm$^{-1}$, 1680 cm$^{-1}$ The propoxyacetylmethylenetriphenylphosphorane, used as starting material, was prepared as follows:

A solution of 1-chloro-3-propoxyacetone (8.5 g.) and triphenylphosphine (15.6 g.) in chloroform (20 ml.) was saturated with nitrogen and heated at reflux under nitrogen overnight. An excess of dry diethyl ether was added, and then the solvents were decanted from the gum that separated. The remaining solvent was removed in vacuo to give crude 2-oxo-3-propoxypropyltriphenylphosphonium chloride (14.9 g). This was stirred vigorously with a solution of sodium carbonate (14.6 g.) in water (146 ml.) for 24 hours. The solution was extracted with diethyl ether and the ethereal extracts dried over sodium sulphate. The solvent was removed by evaporation, and the residue was triturated with petroleum to give propoxyacetylmethylenetriphenylphosphorane (6.3 g.), a sticky solid.

1-Chloro-3-propoxyacetone, used as starting material, was prepared as follows:

8N Jones'reagent [30 ml.; prepared by mixing chromium trioxide (8.0 g.), water (15 ml.) and concentrated sulphuric acid (7.5 ml.) and then dilution with water to 30 ml. volume]was added dropwise to a stirred solution of 1-chloro-2-hydroxy-3-propoxypropane (9.1 g.) in acetone (30 ml.) over a period of 30 minutes, keeping the reaction temperature at 20° C. The mixture was then stirred for 4 hours, and then sufficient water to dissolve the precipitated chromium salts was added. The mixture was extracted three times with diethyl ether and the ether extracts dried over sodium sulphate, concentrated under reduced pressure, redried, and reconcentrated to give crude 1-chloro-3-propoxyacetone (8.5 g.).

vi. Preparation of 7{7-3-(3-oxo-4-propoxybut-1-enyl)-1,4-dioxaspiro[4,4]non-}heptanoic acid Chromium trioxide (9.8 g.) (dried over phosphorus pentoxide) was added portionwise with stirring to a solution of 6-(7-hydroxyhepty)-7-(3-oxo-4-propoxybut-1-enyl)-1,4-dioxaspiro[4,4]nonane (8.6 g.) in dry dimethylformamide (130 ml.) at a temperature lower than 0° C. Concentrated sulphuric acid (3.5 ml.) in dimethylformamide (130 ml.) was added and the mixture stirred at below 10° C. for 1 hour. Diethyl ether was added followed by a minimum quantity of water to produce two readily separable layers. The either layer was separated and stirred with aqueous 2N sodium carbonate solution. The aqueous layer was separated, washed with diethyl ether and then covered with a layer of diethyl ether and acidified to pH 5 by the addition of 20% aqueous sodium dihydrogen phosphate solution. The ethereal layer was separated and the aqueous layer again extracted with diethyl ether. The combined ethereal layers were dried over sodium sulphate and evaporated to give 7-{7-(3-oxo-4-propoxybut-1-enyl)-1,4-dioxaspiro[4,4]-non-6-yl}heptanoic acid (2.1 g.), vii. Preparation of trimethylsilyl 7-{7- (3-oxo-4-propoxybut-1-enyl)-1,4-dioxaspiro[4,4]non-6-yl}heptanoate Hexamethyldisilazane (2.5 ml.) and trimethylchlorosilane (0.5 ml.) were added to a stirred solution of 7-{7-(3-oxo-4-propoxybut-1-enyl))-1,4-dioxaspiro[4,4]-non-6-yl}heptanoic acid (0.5 g.) in dry tetrahydrofuran (30 ml.) and the mixture was stirred at room temperature for 24 hours. The mixture was then filtered and the solvent was removed in vacuo. Xylene (20 ml.) was added and the solvent was again removed in vacuo. This process was repeated twice more, and then petroleum ether (b.p. 60°-80° C.) was added to the residue. The mixture was filtered and the filtrate was concentrated in vacuo to give trimethylsilyl 7-{7-(3-oxo-4-propoxybut-1-enyl)-1,4-dioxaspiro[4,4]non-6-}heptanoate (0.67 g.), $v_{max}$ 860 cm$^{-1}$, 1255 cm$^{-1}$.

viii. Preparation of 7-{7-(3-hydroxy-3-methyl-4-propoxybut-1-enyl)-1,4-dioxaspiro[4,4]non-6-yl}heptanoic acid A solution (1.66 ml.) of methyl magnesium iodide in diethyl ether [prepared in the manner well known in the art from methyl iodide (6 g.), magnesium (1.07 g.) and diethyl ether (20 ml.)]was added dropwise to a stirred solution of trimethylsilyl 7-{7- (3-oxo-4-propoxybut-1-enyl)-1,4-dioxaspiro[4,4]non-6-yl}heptanoate (0.67 g.) in diethyl ether (25 ml.) at room temperature. The mixture was stirred for 30 minutes and a further quantity of the solution of methyl magnesium iodide in diethyl ether (0.4 ml.) was then added dropwise. The mixture was stirred for a further 30 minutes and then added to saturated aqueous ammonium chloride solution (100 ml.) at 0° C. and stirred for 15 minutes. The ether layer was separated and the aqueous layer was extracted with diethyl ether. The combined ether layers were added to 10% w/v aqueous sodium carbonate solution (25 ml.) and stirred for 1 hour. The aqueous layer was separated and washed with diethyl ether, and then acidified to pH 5 by the addition of 20% w/v aqueous sodium dihydrogen phosphate solution. The aqueous layers were again extracted with diethyl ether and the resulting ether extracts dried over sodium sulphate. The solvent was removed in vacuo to give crude 7{7-(3-hydroxy-3-methyl-4-propoxybut-1-enyl)-1,4-dioxaspiro[4,4]non-6-yl}heptanoic acid (0.39 g.).

ix. Preparation of 7-[5-(3-hydroxy-3-methyl-4-propoxybut-1-enyl)-2-oxocyclopentyl]heptanoic acid Crude 7-{7-(3-hydroxy-3-methyl-4-propoxybut-1-enyl)-1,4-dioxaspiro[4,4]non-6-yl}heptanoic acid (0.39 g.) was partly hydrolysed and partly purified by preparative thin-layer chromatography on silica gel, eluting with a 65:15:1 mixture by volume of benzene, dioxan and acetic acid, to give a mixture (60 mg.) of 7{7-(3-hydroxy-3-methyl-4-propoxybut-1-enyl)-1,4-dioxaspiro[4,4]non-6-yl}-heptanoic acid and 7-[5-(3-hydroxy-3-methyl-4-propoxybut-1-enyl)-2-oxocyclopentyl]heptanoic acid. Undried acetone (4 ml.) containing a small amount of water and p-toluenesulphonic acid dihydrate (10 mg.) were added and the mixture was left to stand at room temperature for 24 hours. It was then added to excess diethyl ether and washed with water until the washings were neutral. The ether solution was dried over sodium sulphate and evaporated, to give 7-[5-(3-hydroxy-3-methyl-4-propoxybut-1-enyl)-2-oxocyclopentyl]heptanoic acid, $v_{max}$ 980cm$^{-1}$, 1700 cm$^{-1}$, 1730 cm$^{-1}$; N.M.R. (approximately 10% solution in deuterochloroform): triplet at 0.92δ($J$=7.5 cycles/second), singlet at 1.29δ,multiplets at 1.1 –2.0δ, 2.0 –2.7δ, 3.25 –3.5δ, 5.6 –5.8δ, and a broad singlet at 7.5δ.

EXAMPLE 2

Crude 7-{7-(3-hydroxy-3-methyl-4- propoxybut-1-enyl)-1,4-dioxaspiro[4,4]non-6-yl}heptanoic acid [1.04 g.; prepared as hereinbefore described in Example 1 (viii)], undried acetone (50 ml.) containing a small amount of water and p-toluenesulphonic acid dihydrate (0.1 g.) were left to stand together at room temperature for 24 hours. The mixture was then added to excess diethyl ether and washed with water until the washings were neutral. The ether solution was dried over sodium sulphate and evaporated, to give crude 7-[5-(3-hydroxy-3-methyl-4-propoxybut-1-enyl)-2-oxocyclopentyl]heptanoic acid (0.83 g.). This material was purified by preparative thin layer chromatography on silica gel, using a mixture of toluene, dioxan and acetic acid (65:15:1 by volume) as eluant, to give 7[5-(3-hydroxy-3-methyl-4-propoxybut-1-enyl)2-oxocyclopentyl]heptanoic acid (90 mg.). Elemental analysis: found C, 67.3; H, 9.9%; $C_{20}H_{34}O_5$ requires C, 67.7; H, 9.7%.

EXAMPLE 3

7-[5-(3-Hydroxy-3-methyl-5-ethoxypent-1-enyl)-2-oxocyclopentyl]heptanoic acid i. Preparation of 6-(7-hydroxyheptyl)-7-(3-oxo-5-ethoxypent-1-enyl)-1,4-dioxaspiro[4,4]nonane By proceeding in a similar manner so that described above in Example 1 (v) for the preparation of 6-(7-(3-oxo-4-propoxybut-1enyl)-1,4-dioxaspiro[4,4]nonane, but substituting the appropriate quantity of 3-ethoxypropionylmethylenetriphenylphosphorane for the propoxyacetylmethylenetriphenylphosphorane used as a starting material, there were prepared 6-(7-hydroxyheptyl)-7-(3-oxo-5-ethoxypent-1-enyl)-1,4-dioxaspiro[4,4]-nonane, $v_{max}$ 1620 cm$^{-1}$, 1660 cm$^{-1}$.

The 3-ethoxypropionylmethylenetriphenylphosphorane, used as a starting material, was prepared as follows:

A solution of 1-chloro-4-ethoxybutan-2-one (7.5 g) and triphenylphosphine (13.5 g.) in chloroform (20 ml.) was saturated with nitrogen and heated at reflux under nitrogen overnight. The chloroform was removed in vacuo and the residue was dissolved in dichloromethane (35 ml.). Dry diethyl ether (300 ml.) was added to precipitate 4-ethoxy-2-oxobutyltriphenylphosphonium chloride (19 g.). This compound was added portionwise to a solution of sodium carbonate (10g.) in water (1000 ml.) and the mixture was stirred vigorously for 24 hours. The solution was extracted with diethyl ether, and the ethereal extracts were dried over magnesium sulphate. The solvent was removed by evaporation and the residue was cooled and triturated with petroleum ether (b.p. 60°-80° C.) to give 3-ethoxypropionylmethylenetriphenylphosphorane (10.0 g), m.p. 63°-65° C. Elemental analysis: found C, 76.6; H, 6.5; P, 8.2%; $C_{24}H_{25}O_2P$ requires: C, 76.6; H, 6.7;P 8.3%. 1-Chloro-4-ethoxybutan-2-one, used as starting material, was prepared as follows:

3-Ethoxypropionyl chloride (8.3 g.) was added dropwise at -5° C. to a solution of diazomethane (5.0 g.) in diethyl ether (190 ml.) and the solution was left to stand for 18 hours at room temperature. Hydrogen chloride gas was then bubbled into the solution until it was fully saturated. Crushed ice was added to give approximately 100 ml. of aqueous solution. The organic layer was separated and the aqueous layer was extracted with diethyl ether. The combined organic layers were dried over magnesium sulphate, and evaporated to give crude 1-chloro-4-ethoxybutan-2-one, (7.5 g.).

ii. Preparation of 7-{1,4-dioxa-7-(3-oxo-5-ethoxypent-1-enyl)spiro[4,4]non-6-yl}heptanoic acid By proceeding in a similar manner to that described in Example 1(vi) for the preparation of 7-{7-(3-oxo-4-propoxybut-1-enyl)-1,4-dioxaspiro[4,4]non-6-yl}-heptanoic acid, but substituting the appropriate quantity of 6-(7-hydroxyheptyl)-7-(3-oxo-5-ethoxypent-1-enyl)-1,4-dioxaspiro[4,4]nonane for the 6-(7-hydroxyheptyl)-7-(3-oxo-4-propoxybut-1-enyl)-1,4-dioxaspiro[4,4]nonane used as starting material, there was prepared 7-{1,4-dioxa-7-(3-oxo-5-ethoxypent-1-enyl)spiro[4,4]non-6-yl}-heptanoic acid.

iii. Preparation of trimethylsilyl 7-{1,4-dioxa-7-(3-oxo-5-ethoxypent-1-enyl)spiro[4,4]non-6-yl}-heptanoate By proceeding in a similar manner to that described in Example 1(vii) for the preparation of trimethylsilyl 7-{7-(3-oxo-4-propoxybut-1-enyl)-1,4-dioxaspiro[4,4]non-6-yl}heptanoate, but substituting the appropriate quantity of 7-{1,4-dioxa-7-(3-oxo-5-ethoxypent-1-enyl)spiro[4,4]non-6-yl}heptanoic acid for the 7-{7-(3-oxo-4-propoxybut-1-enyl)-1,4-dioxaspiro[4,4]non-6-yl}heptanoic acid used as starting material, there was prepared trimethylsilyl 7-{1,4-dioxa-7-(3-oxo-5-ethoxypent-1-enyl)spiro[4,4]non-6-yl}heptanoate, $\nu_{max}$ 860 cm$^{-1}$, 1255 cm$^{-1}$.

iv. Preparation of 7-{7-(3-hydroxy-3-methyl-5-ethoxypent-1-enyl)-1,4-dioxaspiro[4,4]non-6-yl}heptanoic acid By proceeding in a similar manner to that described in Example 1(viii) for the preparation of 7-{7-(3-hydroxy-3-methyl-4-propoxybut-1-enyl)-1,4-dioxaspiro[4,4]non-6-yl}heptanoic acid, but substituting the appropriate quantity of trimethylsilyl 7-{1,4-dioxa-7-(3-oxo-5-ethoxypent-1-enyl)spiro[4,4]non-6-yl}heptanoate for the trimethylsilyl 7-{7-(3-oxo-4-propoxybut-1-enyl)-1,4-dioxaspiro[4,4]non-6-yl}heptanoate used as starting material, there was prepared crude 7-{7-(3-hydroxy-3-methyl-5-ethoxypent-1-enyl)-1,4-dioxaspiro[4,4]non-6-yl}heptanoic acid, sufficiently pure for use in the next stage without further purification.

v. Preparation of 7-[5-(3-hydroxy-3-methyl-5-ethoxypent-1-enyl)-2-oxocyclopentyl]heptanoic acid Crude 7-{7-(3-hydroxy-3-5-ethoxypent-1-enyl)-1,4-dioxaspiro[4,4]non-6-yl}heptanoic acid (0.38 g.), water (8 ml.) and glacial actic acid (16 ml.) were left to stand at room temperature for 6 hours. The solution was then evaporated in vacuo at a temperature lower than 50° C. Ethyl acetate (150 ml.) was added, and then the solution washed with water (until the pH of the washings was pH 5), dried over sodium sulphate, and evaporated to give 7-[5-(3-hydroxy-3-methyl-5-ethoxypent-1-enyl)-2-oxocyclopentyl]heptanoic acid (0.36 g.), $\nu_{max}$ 980 cm$^{-1}$, 1700 cm$^{-1}$, 1730 cm$^{-1}$.

EXAMPLE 4 Methyl 7-[5-(3-hydroxy-3-methyl-5-ethoxypent-1-enyl)-2-oxocyclopentyl]heptanoate 7-[5-(3-Hydroxy-3-methyl-5-ethoxypent-1-enyl)-2-oxocyclopentyl]heptanoic acid (0.24 g.) was diluted with hexamethylphosphotriamide (1.8 ml.) and treated with aqueous sodium hydroxide solution (25% w/v; 0.163 ml.). After stirring for two hours at room temperature, methyl iodide (0.177 ml.) was added and stirring continued for a further 24 hours. The reaction mixture was extracted twice with diethyl ether and the combined ethereal extracts were washed twice with water and dried over anhydrous sodium sulphate. Evaporation gave crude methyl 7-[5-(3-hydroxy-3-methyl-5-ethoxypent-1-enyl)-2-oxocyclopentyl]heptanoate (0.17 g.) as the residue. This was purified by preparative thin-layer chromatography on silica gel, using mixture of toluene, dioxan and acetic acid (65:15:1 by volume) as eluant, to give methyl 7-[5-(3-hydroxy-3-methyl-5-ethoxypent-1-enyl)-2-oxocyclopentyl]- heptanoate (30 mg.). Elemental analysis: found: C, 68.3; H, 10.1%; $C_{21}H_{36}O_5$ requires: C, 68.5; H, 9.9%. N.M.R. (approximately 10% solution in deuterochloroform): triplet at 1.2δ (J=7 cycles/sec.), singlet at 1.3δ, multiplets at 1.0–2.0δ, 2.0–2.5δ, 3.2–3.75δ, singlet at 3.6δ, and multiplet at 5.6–5.8δ.

EXAMPLE 5
7-[5-(3-Hydroxy-6-methoxy-3-methylhex-1-enyl)-2-oxocyclopentyl]heptanoic acid i. Preparation of 6-(7-hydroxyheptyl)-7-(6-methoxy-3-oxohex-1-enyl)-1,4-dioxaspiro[4,4]nonane A solution of dimethyl 5-methoxy-2-oxopentylphosphonate (5.3 g.) in tetrahydrofuran (19 ml.) was added to a stirred suspension of sodium hydride (0.39 g.) in tetrahydrofuran (140 ml.). The mixture was stirred at room temperature until the evolution of hydrogen had ceased, then treated dropwise with a solution of 7-formyl-6-(7-hydroxyheptyl)-1,4-dioxaspiro[4,4]nonane [4.8 g.; prepared as described in Example 1(iv)]in tetrahydrofuran (47 ml.) and stirred for a further 2 hours. The mixture was acidified to pH 4 by the addition of glacial acetic acid, the solvents were removed in vacuo and diethyl ether was added to the residue. The solid was filtered off and the filtrate was washed with aqueous sodium carbonate, dried over anhydrous sodium sulphate, and evaporated to dryness, to give 6-(7-hydroxyheptyl)-7-(6-methoxy-3-oxohex-1-enyl)-1,4-dioxaspiro[4,4]nonane (6.4 g.), $\nu_{max}$ 1620 cm$^{-1}$, 1660 cm$^{-1}$.

The dimethyl 5-methoxy-2-oxopentylphosphonate, used as a starting material in the above preparation, was prepared by treating dropwise, during 20 minutes, a stirred solution of dimethyl methylphosphonate (24.8 g.) in dry tetrahydrofuran (175 ml.) at −45° C. to −60° C., under nitrogen, with a solution of butyl lithium (16 g.) in n-hexane (162 ml.). Stirring was continued at that temperature for a further 10 minutes, and then the mixture was cooled to −60° C. and treated, dropwise during 10 minutes, with a solution of n-propyl 4-methoxybutyrate (16.0 g.) in tetrahydrofuran (50 ml.). The mixture was stirred at −60° C. for a further 90 minutes and then at room temperature for 3 hours, and then it was treated with glacial acetic acid (20 ml.), concentrated in vacuo, and the residue treated with water (100 ml.). The mixture was extracted twice with methylene chloride, and the combined methylene chloride solutions were washed with water, dried over sodium sulphate and concentrated in vacuo. The residue was distilled, to give dimethyl 5-methoxy-2-oxopentylphosphonate (8.6 g.), b.p. 122°–128° C./0.07 mm.Hg.

ii. Preparation of 7-{7-(6-methoxy-3-oxohex-1-enyl)-1,4-dioxaspiro[4,4]non-6-yl}heptanoic acid By proceeding in a similar manner to that described in Example 1(iv) for the preparation of 7-{7-(3-oxo-4-propoxybut-1-enyl)-1,4-dioxaspiro[4,4]non-6-yl}heptanoic acid, but substituting the appropriate quantity of 6-(7-hydroxyheptyl)-7-(6-methoxy-3-oxohex-1-enyl)-1,4-dioxaspiro[4,4]nonane for the 6-(7-hydroxyheptyl)-7-(3-oxo-4-propoxybut-1-enyl)-1,4-dioxaspiro[4,4]- nonane, used as starting material, there was prepared 7-{7-(6-methoxy-3-oxohex-1-enyl)-1,4-dioxaspiro[4,4]-non-6-yl}heptanoic acid.

iii. Preparation of trimethylsilyl 7-{7-(6-methoxy-3-oxohex-1-enyl)-1,4-dioxaspiro[4,4]non-6-yl}-heptanoate By proceeding in a similar manner to that described in Example 1(vii) for the preparation of trimethylsilyl 7-{7-(3-oxo-4- propoxybut-1-enyl)-1,4-dioxaspiro[4,4]-non-6-yl}heptanoate, but substituting the appropriate quantity of 7-{7-(6-methoxy-3-oxohex-1-enyl)-1,4-dioxaspiro[4,4]non-6-yl}heptanoic acid for the 7-{7-(3-oxo-4-propoxybut-1-enyl)-1,4-dioxaspiro[4,4]non-6-yl}heptanoic acid used as starting material, there was prepared trimethylsilyl 7-{7-(6-methoxy-3-oxohex-1-enyl)-1,4-dioxaspiro[4,4]non-6-yl}heptanoate, $v_{max}$ 860 cm$^{-1}$, 1255 cm$^{-1}$.

iv. Preparation of 7-{7-(3-hydroxy-6-methoxy-3-methylhex-1-enyl)-1,4-dioxaspiro[4,4]non-6-yl}heptanoic acid By proceeding in a similar manner to that described in Example 1(viii) for the preparation of 7-{7-(3-hydroxy-3-methyl-4-propoxybut-1-enyl)-1,4-dioxaspiro[4,4]non-6-yl}heptanoic acid, but substituting the appropriate quantity of trimethylsilyl 7-{7-(6-methoxy-3-oxohex-1-enyl)-1,4-dioxaspiro[4,4]non-6-yl}-heptanoate for the trimethylsilyl 7-{7-(3-oxo-4-propoxybut 1-enyl)-1,4-dioxaspiro[4,4]non-6-yl}heptanoate used as starting material, there was prepared 7-{7-(3-hydroxy-6-methoxy-3-methylhex-1-enyl)-1,4-dioxaspiro[4,4]non-6-yl}heptanoic acid v. Preparation of 7-[5-(3-hydroxy-6-methoxy-3-methylhex-1-enyl)-2-oxocyclopentyl]heptanoic acid By proceeding in a similar manner to that described in Example 3(v) for the preparation of 7-[5-(3-hydroxy-3-methyl-5-ethoxypent-1-enyl)-2-oxocyclopentyl]heptanoic acid, but substituting the appropriate quantity of 7-{7-(3-hydroxy-6-methoxy-3-methylhex-1-enyl)-1,4-dioxaspiro[4,4]non-6-yl}heptanoic acid for the 7-{7-(3-hydroxy-3-methyl-5-ethoxypent-1-enyl)-1,4-dioxaspiro[4,4]non-6-yl}heptanoic acid used as starting material, there was prepared 7-[5-(3-hydroxy-6-methoxy-3-methylhex-1-enyl(-2-oxocyclopentyl]heptanoic acid, $v_{max}$ 980 cm$^{-1}$, 1700 cm$^{-1}$, 1730 cm$^{-1}$.

EXAMPLE 6 Methyl 7-[5-(3-hydroxy-6-methoxy-3-methylhex-1-enyl)-2-oxocyclopentyl]heptanoate By proceeding in a similar manner to that described in Example 4 for the preparation of methyl 7-[5-(3-hydroxy-3-methyl-5ethoxypent-1-enyl)2-oxocyclopentyl]heptanoate, but substituting the appropriate quantity of 7-[5-(3-hydroxy-6-methoxy-3-methylhex-1-enyl)-2-oxocyclopentyl]heptanoic acid for the 7-[5-(3-hydroxy3-methyl-5-ethoxypent-1-enyl)-2-oxocyclopentyl]heptanoic acid used as starting material, there was prepared methyl 7-[5-(3-hydroxy-6-methoxy-3-methylhex-1-enyl)-2-oxocyclopentyl]heptanoate. Elemental analysis: found: C, 68.3; H, 10.2%; $C_{21}H_{36}O_5$ requires C, 68.5; H, 9.9%. $v_{max}$ 980 cm$^{-1}$, 1700 cm$^{-1}$, 1735 cm$^{-1}$, 3500 cm$^{-1}$. N.M.R. (approximately 10% solution in deuterochloroform): multiplets at 1.0–2.0δ, 2.0–2.8δ, 3.4δ, singlets at 3.35δ, 3.8δ and a multiplet at 5.6δ.

The present invention includes within its scope pharmaceutical compositions which comprise at least one compound of the above-mentioned novel class of cyclopentane derivatives of general formula I or, when $R^4$ represents a hydrogen atom, a non-toxic salt thereof, together with a pharmaceutical carrier or coating. In clinical practice the novel compounds of the present invention will normally be administered orally, rectally, vaginally or parenterally.

Solid compositions for oral administration include compressed tablets, pills, dispersible powders, and granules. In such solid compositions one or more of the active compounds is, or are, admixed with at least one inert diluent such as calcium carbonate, potato starch, alginic acid, or lactose. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing one or more of the active substances with or without the addition of diluents or excipients.

Solid compositions for vaginal administration include pessaries formulated in manner known per se and containing one or more of the active compounds.

Solid compositions for rectal administration include suppositories formulated in manner known per se and containing one or more of the active compounds.

Preparations according to the invention for parenteral adminstration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compositions, by irradiation, or by heating. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment. In the adult, the doses are generally between 0.02 and 2.0 mg. by aerosol administration as bronchodilators, between 0.0002 and 2.0 mg./kg. body weight by intravenous administration, preferably by intravenous infusion at a rate of between 0.0001 and 1.0 mg./kg. body weight/minute as hypotensives, between 0.001 and 0.3 mg./kg. body weight orally as inhibitors of gastric acid secretion and between 0.01 and 1.0 mg./kg. body weight by intravenous administration, preferably by intravenous infusion at a rate of between 0.02 and 20 μg./kg. body weight/minute as stimulators of uterine contraction. If necessary these doses may be repeated as and when required.

The compounds of general formula I and, when $R^4$ represents a hydrogen atom, non-toxic salts thereof may be administered orally as bronchodilators by any method known per se for administration by inhalation of drugs which are not themselves gaseous under normal conditions of administration. Thus, a solution of the active ingredient in a suitable pharmaceutically-acceptable solvent, for example water, can be nebulized by a mechanical nebulizer, for example a Wright Nebulizer, to give an aerosol of finely-divided liquid particles suitable for inhalation. Advantageously, the solution to be nebulized is diluted, and aqueous solutions containing from 0.2 to 20 mg., and preferably 0.2 to 5.0 mg., of active ingredient per ml. of solution are particularly suitable. The solution may contain stabilizing agents such as sodium bisulphite and buffering agents to give it an isotonic character, e.g. sodium chloride, sodium citrate and citric acid.

The active ingredients may also be administered orally by inhalation in the form of aerosols generated from self-propelling pharmaceutical compositions. Compositions suitable for this purpose may be obtained by dissolving or suspending in finely-divided from, preferably micronized to an average particle size of less than 5 microns, the active ingredients in pharmaceutically-acceptable solvents, e.g. ethanol, which are co-solvents assisting in dissolving the active ingredients in the volatile liquid propellants hereinafter described, or pharmaceutically-acceptable suspending or dispersing agents, for example aliphatic alcohols such as oleyl alcohol, and incorporating the solutions or suspensions obtained with pharmaceutically-acceptable volatile liquid propellants, in conventional pressurized packs which may be made of any suitable material, e.g. metal, plastics or glass, adequate to withstand the pressures generated by the volatile propellant in the pack. Pressurized pharmaceutically-acceptable gases, such as nitrogen, may also be used as propellants. The pressurized pack is preferably fitted with a metered valve which dispenses a controlled quantity of the self-propelling aerosol composition as a single dose.

Suitable volatile liquid propellants are known in the art and include fluorochlorinated alkanes containing from one to four, and preferably one or two, carbon atoms, for example dichlorodifluoromethane, dichlorotetrafluoroethane, trichloromonofluoromethane, dichloromonofluoromethane and monochlorotrifluoromethane. Preferably, the vapour pressure of the volatile liquid propellant is between about 25 and 65 pounds, and more especially between about 30 and 55 pounds, per square inch gauge at 21° C. As is well-known in the art, volatile liquid propellants of different vapour pressures may be mixed in varying proportions to give a propellant having a vapour pressure appropriate to the production of a satisfactory aerosol and suitable for the chosen container. For example dichlorodifluoromethane (vapour pressure 85 pounds per square inch gauge at 21° C.) and dichlorotetrafluoroethane (vapour pressure 28 pounds per square inch gauge at 21° C.) may be mixed in varying proportions to give propellants having vapour pressures intermediate between those of two constituents, e.g. a mixture of dichlorodifluoromethane and dichlorotetrafluoroethane in the proportions 38:62 respectively by weight has a vapour pressure of 53 pounds per square inch gauge at 21° C.

The self-propelling pharmaceutical compositions may be prepared by dissolving the required quantity of active ingredient in the co-solvent or combining the required quantity of active ingredient with a measured quantity of suspending or dispersing agent. A measured quantity of this composition is then placed in an open container which is to be used as the pressurized pack. The container and its contents are then cooled below the boiling temperature of the volatile propellant to be used. The required quantity of liquid propellant, cooled below its boiling temperature, is then added and the contents of the container mixed. the container is then sealed with the required valve fitting, without allowing the temperature to rise above the boiling temperature of the propellant. The temperature of the sealed container is then allowed to rise to ambient with shaking to ensure complete homogeneity of the contents to give a pressurized pack suitable for generating aerosols for inhalation. Alternatively, the co-solvent solution of the active ingredient or combination of active ingredient and suspending or dispersing agent is placed in the open container, the container sealed with a valve, and the liquid propellant introduced under pressure.

Means for producing self-propelling compositions for generating aerosols for the administration of medicaments are, for example, described in detail in U.S Pat. Nos. 2,868,691 and 3,095,355.

Preferably, the self-propelling pharmaceutical compositions according to the present invention contain from 0.2 to 20 mg., and more particularly 0.2 to 5.0 mg., of active ingredient per ml. of solution or suspension. It is important that the pH of solutions and suspensions used, according to the present invention, to generate aerosols should be kept within the range 3 to 8 and preferable that they should be stored at or below 4° C., to avoid pharmacological deactivation of the active ingredient.

In carrying out the present invention, the means of producing an aerosol for inhalation should be selected in accordance with the physico-chemical properties of the active ingredient.

By the term "pharmaceutically-acceptable" as applied in this specification to solvents, suspending or dispersing agents, propellants and gases is meant solvents, suspending or dispersing agents, propellants and gases which are non-toxic when in aerosols suitable for inhalation therapy.

It is highly desirable that the aerosols should have a particle size less than about 10 microns and preferably less than 5 microns, for example between 0.5 and 3 microns, to ensure effective distribution to very narrow bronchioles. Preferably, administration is by means of devices enabling controlled quantities of the active ingredients to be administered, for example by means of the metered valves hereinbefore mentioned.

The following Example illustrates pharmaceutical compositions according to the invention.

EXAMPLE 7

7-[5-(3-Hydroxy-3-methyl-4-propoxybut-1-enyl)-2-oxocyclopentyl]heptanoic acid (300 mg.) was dissolved in ethanol (1 ml.) and the solution obtained was added to an aqueous solution (12 ml.) containing sodium carbonate (50 mg.). Aqueous sodium chloride solution (0.9% w/v; 2 ml.) was then added to give a final volume of 15 ml. The solution was then sterilised by passage

We claim:
1. A cyclopentane derivative of the formula:

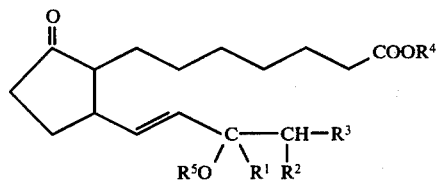

wherein $R^1$ represents alkyl of 1 through 4 carbon atoms, $R^2$ represents hydrogen or alkyl of 1 through 3 carbon atoms, $R^3$ represents alkoxy of 3 through 6 carbon atoms, $R^4$ represents hydrogen or alkyl of 1 through 12 carbon atoms and $R^5$ represents hydrogen or alkyl of 1 through 4 carbon atoms or a carboxylic acyl group and, where $R^4$ represents a hydrogen atom, non-toxic pharmaceutically-acceptable salts thereof.

2. A cyclopentane derivative according to claim 1 wherein $R^5$ represents hydrogen, and $R^1$, $R^2$, $R^3$ and $R^4$ are as defined in claim 1.

3. A cyclopentane derivative according to claim 1 wherein $R^3$ represents alkoxy of 3 carbon atoms, $R^5$ represents hydrogen, and $R^1$, $R^2$ and $R^4$ are as defined in claim 1.

4. A cyclopentane derivative according to claim 1 wherein $R^1$ represents methyl, $R^2$ represents hydrogen, $R^3$ represents alkoxy of 3 carbon atoms, and $R^4$ and $R^5$ are as defined in claim 1.

5. The cyclopentane derivative according to claim 1 which is 7-[5-(3-hydroxy-3-methyl4-propoxybut-1-enyl)-2-oxocyclopentyl]heptanoic acid, and non-toxic pharmaceutically-acceptable salts thereof, and alkyl esters thereof containing 1 through 12 carbon atoms in the alkyl radical.

6. A pharmaceutical composition useful for the production of hypotension, which comprises, as active ingredient, at least one cyclopentane derivative as claimed in claim 1, or in the case of an acid a non-toxic pharmaceutically-acceptable salt thereof, in association with a pharmaceutical carrier or coating.

7. A pharmaceutical composition useful for bronchodilatation, which comprises, as active ingredient, at least one cyclopentane derivative as claimed in claim 1, or in the case of an acid a non-toxic pharmaceutically-acceptable salt thereof, in association with a pharmaceutical carrier or coating.

8. A pharmaceutical composition useful for inhibition of gastric acid secretion, which comprises, as active ingredient, at least one cyclopentane derivative as claimed in claim 1, or in the case of an acid a non-toxic pharmaceutically-acceptable salt thereof, in association with a pharmaceutical carrier or coating.

9. A pharmaceutical composition useful for stimulation of uterine contraction, which comprises, as active ingredient, at least one cyclopentane derivative as claimed in claim 1, or in the case of an acid a non-toxic pharmaceutically-acceptable salt thereof, is association with a pharmaceutical carrier or coating.

* * * * *